(12) United States Patent
Heaton et al.

(10) Patent No.: US 11,027,109 B2
(45) Date of Patent: Jun. 8, 2021

(54) CONNECTOR FOR A MEDICAL DEVICE

(71) Applicant: i2r Medical Limited, Bournemouth (GB)

(72) Inventors: Keith Patrick Heaton, Bournemouth (GB); Ian James Hardman, Bournemouth (GB)

(73) Assignee: i2r Medical Limited, Bournemouth (GB)

(*) Notice: Subject to any disclaimer, the term of this patent is extended or adjusted under 35 U.S.C. 154(b) by 90 days.

(21) Appl. No.: 15/771,407

(22) PCT Filed: Nov. 3, 2016

(86) PCT No.: PCT/GB2016/053423
§ 371 (c)(1),
(2) Date: Apr. 27, 2018

(87) PCT Pub. No.: WO2017/077312
PCT Pub. Date: May 11, 2017

(65) Prior Publication Data
US 2018/0345001 A1 Dec. 6, 2018

(30) Foreign Application Priority Data

Nov. 3, 2015 (GB) .................................... 1519388

(51) Int. Cl.
*A61M 39/10* (2006.01)
*A61M 1/00* (2006.01)
*A61M 39/24* (2006.01)
(52) U.S. Cl.
CPC .......... *A61M 39/10* (2013.01); *A61M 1/0033* (2014.02); *A61M 1/0086* (2014.02);
(Continued)

(58) Field of Classification Search
CPC .. A61M 39/10; A61M 1/0033; A61M 1/0086; A61M 1/0088; A61M 39/24;
(Continued)

(56) References Cited

U.S. PATENT DOCUMENTS

2011/0224633 A1* 9/2011 Robinson ............ A61M 1/0031
604/319
2012/0184931 A1 7/2012 Horn
(Continued)

FOREIGN PATENT DOCUMENTS

WO WO 2011087871 7/2011

OTHER PUBLICATIONS

International Preliminary Report on Patentability in related application PCT/GB2016/053423, dated May 8, 2018, 9 pages.
(Continued)

*Primary Examiner* — Lauren P Farrar
(74) *Attorney, Agent, or Firm* — Bochner IP; Andrew D. Bochner

(57) ABSTRACT

The present invention provides a wound dressing tubing connector, comprising a first unit and a second unit which are releasably connectable and which when connected form a fluid path through the connector, wherein the first unit comprises an inlet and an outlet and wherein the second unit comprises an inlet and an outlet, in which the outlet of the first unit and the inlet of the second unit when connected together define the fluid path, and wherein the first unit and the second unit are connectable to form an air and fluid tight seal and wherein the first unit and/or the second unit comprises a pressure regulator valve in fluid communication with the fluid path. Also provided are systems, kits and methods of treatment.

19 Claims, 5 Drawing Sheets

(52) U.S. Cl.
CPC .......... *A61M 1/0088* (2013.01); *A61M 39/24* (2013.01); *A61M 2039/1027* (2013.01); *A61M 2039/1033* (2013.01); *A61M 2039/2473* (2013.01)

(58) Field of Classification Search
CPC .. A61M 2039/1027; A61M 2039/1033; A61M 2039/2473
See application file for complete search history.

(56) References Cited

U.S. PATENT DOCUMENTS

| | | | |
|---|---|---|---|
| 2012/0271256 A1 | 10/2012 | Locke et al. | |
| 2013/0131616 A1 | 5/2013 | Locke | |
| 2013/0172837 A1* | 7/2013 | Kenny | A61M 1/0031 |
| | | | 604/319 |
| 2015/0094674 A1* | 4/2015 | Pratt | A61F 13/00068 |
| | | | 604/318 |
| 2016/0346485 A1* | 12/2016 | Mohr | A61M 5/385 |

OTHER PUBLICATIONS

International Search Report in related application PCT/GB2016/053423, dated May 11, 2017, 6 pages.

\* cited by examiner

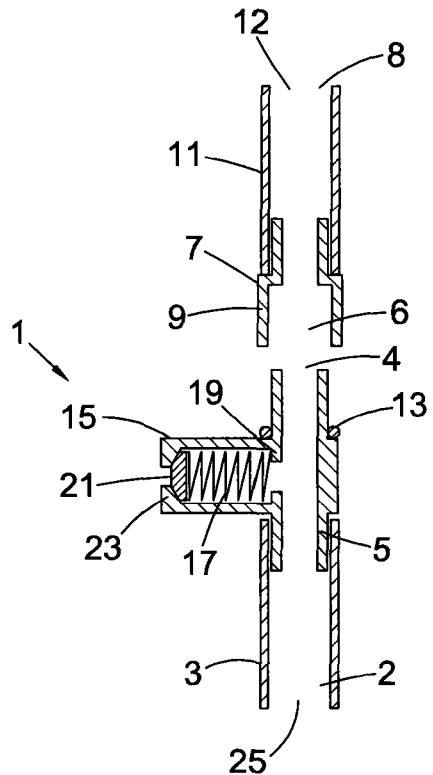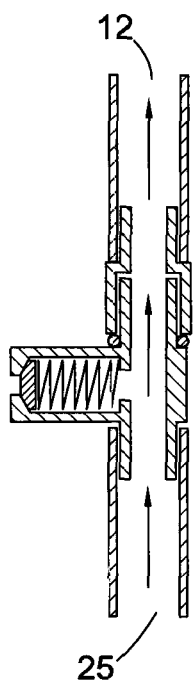
Fig. 1　　　　Fig. 2
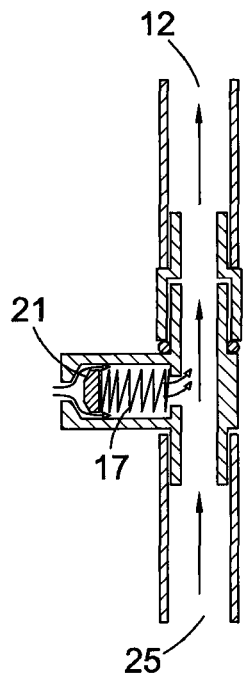
Fig. 3

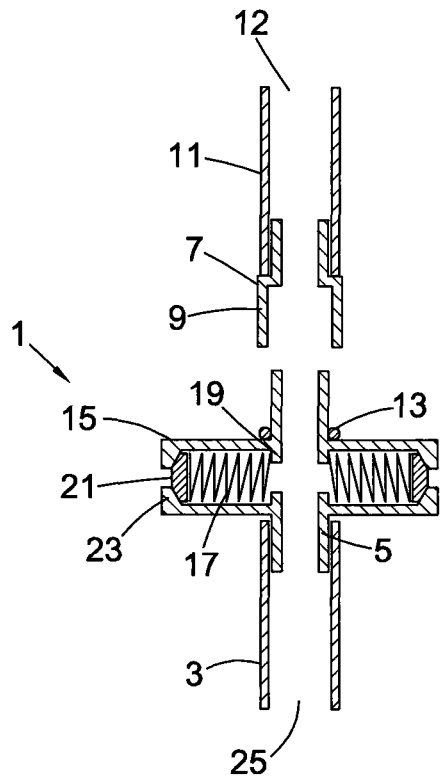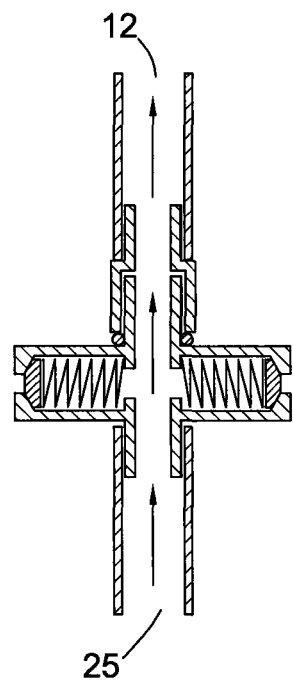
Fig. 4    Fig. 5
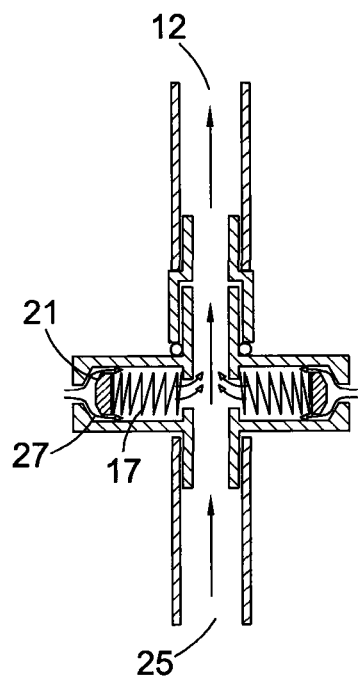
Fig. 6

CONNECTOR FOR A MEDICAL DEVICE

The present invention relates to a system for providing pressure control in an apparatus for use in Negative Pressure Wound Therapy, a connector for use in such a system as well as a connection kit.

Negative Pressure Wound Therapy (NPWT), Reduced Pressure Therapy or Sub-Atmospheric Pressure Therapy is used to treat hard to heal wounds and works on the principle of applying a sub-atmospheric pressure (normally between 50 mmHg and 200 mmHg gauge pressure) to a porous dressing situated at the wound site.

Typically the porous dressing would be held in place with a partially occlusive adhesive film and a tube connects the dressing assembly to a rigid fluid container fitted to the pressure generating device, which consists of a low flow vacuum pump, a receptacle for the fluid container, a control system and a moulding to house the various components. In a typical device in clinical use a control system energises the pump which in turn evacuates the dressing and draws air and fluid out of the wound dressing site via the tube into the rigid container. When the air has been evacuated a negative pressure is established at the wound site which is communicated back to the container inside the pump unit housing via the tubing, this in turn is communicated to the control system within the unit housing. The control system regulates the vacuum pump to maintain the required set pressure. Examples of NPWT systems in clinical use are the Info V.A.C® manufactured by KCl of San Antonio, Tex., USA and Renasys™ system manufactured by Smith and Nephew of Hull, UK.

Conventional methods of controlling the negative pressure at the wound site in NPWT devices has been through the use of electronic pressure sensors measuring pressure at the pump, inside the waste fluid canister or with the use of multi-lumen tubing at the wound site. The pressure sensor values are compared to the required target pressure selected by the user and then the control software adjusts the pump speed or in some cases utilises a solenoid valve to open to atmospheric pressure.

Monitoring and control of pressure at the wound site is achieved in several different ways by commercial devices currently on the market. KCl (San Antonio, Tex.) utilises a technology called T.R.A.C™. This consists of a multi-lumen tube consisting of a fluid path and sensing lumens which transmit the pressure at the wound site to a pressure sensing circuit in the product housing.

Other commercial devices utilise a system that measures pressure inside the fluid container on the wound side of the protective hydrophobic filter. The pressure feedback control electronics then regulates the pump power to meet the target pressure.

Other commercial systems provide a fixed bleed within the pneumatic system to stimulate flow and aid pressure control. GB-A-2508696 describes an apparatus and system for providing NWPT where the pressure regulator valve is attached to the wound dressing via tubing.

To ensure effective therapy is delivered a relatively constant negative pressure at the wound site needs to be maintained. If the pressure at the wound site is not accurately controlled then this can lead to a series of problems including inconsistent wound healing, pain and in extreme cases bleeding. As well as accurate pressure control there is also a need to maintain a minimum level of flow from the wound site. Potentially with a sealed dressing then a situation can exist where is there is little or no flow from the wound site to the wound fluid container.

This can lead to the wound exudate "pooling" at the wound site which can lead to a series of problems including breakdown of the seal of the covering film to the skin, maceration of the periwound skin area and potentially an increase in infection at the wound site. Maintaining consistent pressure and flow at the wound site becomes increasingly important with patients who have been discharged from hospital with complex wounds. However increased mobility leads to additional difficulties in controlling pressure and flow rates at the wound site which does not always occur in hospital situations when the patients are lying down and relatively immobile. One particular issue is the potential height difference that can exist between the pump and the wound site, which is often the case when a leg or foot ulcer is being treated. This can result in a pressure difference of up to 75 mmHg depending on the length of tubing used which is due to the hydrostatic pressure present on the wound fluid. If the system is controlling pressure within the pump control unit this can result in a reduced pressure at the wound resulting in reduced therapeutic effectiveness and compromised wound fluid drainage. Similarly moving the pump unit below the wound can in some cases result in a spike of pressure.

Pressure control in traditional NPWT devices is achieved by the use of pressure transducers measuring pressure within the pump unit and comparing it with the desired pressure. The pump pressure is then adjusted via the electronic control system to match the actual pressure at the measurement point to the desired set pressure.

Problems with this arrangement include the discrepancy between the pressure measured at the pump unit and the actual pressure at the wound site. This discrepancy can be caused by the pressure drop across the protective hydrophobic filter or a height difference between the pump unit and the dressing as described above or the viscosity of the wound fluid. The pressure discrepancy between the pump unit and the dressing can be compensated by having a second pressure transducer sensing pressure at the wound side of the filter or at the wound dressing itself. However this requires complex arrangements of tubing separating the air path from the fluid path, a second pressure transducer, a safety release solenoid and electronics to receive and condition the signal from the transducers and a software algorithm to convert this into an output signal that will drive the pump at the correct level to achieve the target pressure.

There is therefore a need for improved systems and devices which can provide NPWT to patients.

According to a first aspect of the invention there is provided a wound dressing tubing connector, comprising a first unit and a second unit which are releasably connectable and which when connected form a fluid path through the connector, wherein the first unit comprises an inlet and an outlet and wherein the second unit comprises an inlet and an outlet, in which the outlet of the first unit and the inlet of the second unit when connected together define the fluid path, and wherein the first unit and the second unit are connectable to form an air and fluid tight seal and wherein the first unit and/or the second unit comprises a pressure regulator valve in fluid communication with the fluid path.

The pressure regulator valve may be of any suitable construction for attachment to the first unit and/or second unit and for fluid communication with the fluid path.

The pressure regulator valve may be connected directly or indirectly to the fluid path. When connected directly to the fluid path, at least a portion of the pressure regulator valve may be adjacent to the fluid path. For example, the pressure regulator valve may be connected to the fluid path via a parallel path within the connector wherein the parallel path is in fluid communication with the fluid path.

In some embodiments there is provided a wound dressing tubing connector, comprising a first unit and a second unit which are releasably connectable and which when connected form a fluid path through the connector, wherein the first unit comprises an inlet and an outlet and wherein the second unit comprises an inlet and an outlet, in which the outlet of the first unit and the inlet of the second unit when connected together define the fluid path, and wherein the first unit and the second unit are connectable to form an air and fluid tight seal and wherein the first unit and/or the second unit comprises a pressure regulator valve. The pressure regulator valve may be arranged to be fluidly coupled to the fluid path, for example using tubing external to the connector.

The pressure regulator valve may be fluidly connected to a separate conduit that runs in parallel to at least a portion of the fluid path. The separate conduit or pressure regulator may interconnect to the fluid path externally to the connector, optionally at the wound site. The separate conduit may also be referred to as a parallel path, an air pathway or air path.

The separate conduit may have a first terminus at the pressure regulator valve and a second terminus at a fluid coupling.

As used herein, the term "fluid coupling" may be used interchangeably with the term "fluid port" or "air port".

In some embodiments, the pressure regulator valve may be placed in fluid communication with the fluid path by connection of the fluid coupling to the fluid path. The connection to the fluid path may be made using a tube. The connection to the fluid path may be a connection of the fluid coupling to the inlet of the first unit or the outlet of the second unit. The connection of the fluid coupling to the inlet of the first unit or the outlet of the second unit may be direct or indirect. For example, the fluid coupling may be indirectly connected to the inlet of the first unit via the wound dressing, such as where the wound dressing is positioned at an intermediate point in the path between the pressure regulator valve and the fluid path defined by the first and second unit.

Accordingly, the pressure regulator valve may be placed in fluid communication with the fluid path by connection of a fluid coupling to the inlet of the first unit via the wound dressing.

The pressure regulator valve may be fluidly connected to the fluid path via a separate conduit that runs in parallel to at least a portion of the fluid path. The separate conduit may also be referred to as a parallel path, an air pathway or air path.

The air pathway may have a first terminus at the pressure regulator valve in the connector and a second terminus at the wound dressing and/or on the fluid path between the connector and the wound dressing and/or on the fluid path between the connector and the pump. The pressure regulator valve may be in fluid communication with the fluid path via the wound dressing. Thus, the pressure regulator valve may be connected to the fluid path via a parallel path which may be at least partially exterior to the connector.

A configuration where the parallel path connects the pressure regulator valve to the fluid path via the wound dressing is an example of the pressure regulator valve being connected indirectly to the fluid path.

The phrases "parallel path" and "runs in parallel" as used herein refer to the presence of two or more paths or conduits through which fluid (including air) may flow. It will be understood that these phrases are not used in a mathematical or geometric sense, such that the "parallel path" and the fluid path do not necessarily remain the same distance apart along their entire lengths.

Accordingly, the connector may be arranged to be attached to the wound dressing via two or more tubes, for example a tube for fluid and one or more tubes for air. The tube for air and the tube for fluid may be combined into a tube for fluid with separate pathways. For example, a multi-lumen tube may be used. Use of a single tube with separate pathways may make the connector more convenient to use. Accordingly, the connector may comprise one or more fluid couplings arranged to connect to one or more tubes for air. The tube for fluid may alternatively be termed the inlet tube or conduit, or the fluid inlet tube or conduit. The one or more tubes for air may alternatively be termed the one or more air inlet tubes or conduits since in use they carry air which has been let into the connector via the pressure regulator valve towards the wound. Alternatively, the one or more tubes for air may be termed the one or more air outlet tubes or conduits since in use they may carry out of the connector the air that has entered the connector via the pressure regulator valve. Since air is a fluid, the pressure regulator valve is nevertheless in fluid communication with the fluid path.

The air path may pass through the first unit and/or the second unit of the connector. Accordingly, the first and/or the second unit may comprise a fluid coupling arranged to connect to one or more tubes for air. The fluid coupling may be arranged to permit the air path to pass out of the first unit and/or the second unit. Typically, the air path will pass out of from the first unit via the fluid coupling. Accordingly, the first unit will typically comprise the fluid coupling. The first and/or second unit may comprise one or more fluid couplings.

The "separate conduit" or "air pathway" described above may alternatively be termed the "parallel path", "air path" or the "second fluid path". When the air pathway is described as the "second fluid path" the fluid path may be described as the "first fluid path".

The pressure regulator valve may be configured to possess an open and a closed state. The transition between the open and closed state may be controlled by an internal control means or an external control means.

The pressure regulator valve may be a non-electrical pressure regulator valve. A non-electrical pressure regulator valve may be configured to possess an open and a closed state. The transition between the open and closed state may be automatically triggered.

The pressure regulator valve may be configured, when activated, to provide a fluid conduit between the fluid path and atmosphere. The fluid conduit may allow the passage of air into the fluid path. The fluid conduit may be gated.

Air may pass through the fluid conduit into the fluid path directly or indirectly. For example, the connector may comprise a parallel pathway arranged to air to pass indirectly from the fluid conduit to the fluid path.

The pressure regulator valve may be configured to be activated when the pressure within the fluid path falls below a predetermined value, or the pressure differential between atmosphere and the fluid path exceeds a predetermined value.

Optionally, the pressure regulator valve comprises a sealing means configured to reversibly occlude the fluid conduit with atmosphere. The sealing means may act to gate the fluid conduit. The sealing means may be a sealing system of any suitable construction. The sealing means may for example be a seal element. The sealing means or seal element may, for example, be a plug or a plunger.

The pressure regulator valve may comprise a passive control means for controlling activation of the valve. Optionally, the pressure regulator valve comprises a passive control means wherein the sealing means is configured to reversibly occlude the fluid conduit by means of the passive control means. The passive control means may be of any suitable construction and may gate the fluid conduit with atmosphere. The passive control means may trigger the occlusion of the fluid conduit by triggering a transition for from the open state of the valve to the closed state. Conversely, a passive control means may trigger the de-occlusion of the fluid conduit by triggering a transition for from the closed state of the valve to the open state. The passive control means may be configured to be responsive to a pressure gradient across the pressure regulator valve.

Optionally, the pressure regulator valve comprises an internal control means wherein the sealing means is configured to reversibly occlude the fluid conduit by means of the internal control means. The internal control means may be of any suitable construction and may gate the fluid conduit with atmosphere. The internal control means may trigger the occlusion of the fluid conduit by triggering a transition for from the open state of the valve to the closed state. Conversely, an internal control means may trigger the de-occlusion of the fluid conduit by triggering a transition for from the closed state of the valve to the open state. The internal control means may be configured to be responsive to a pressure gradient across the pressure regulator valve.

Optionally, the sealing means is configured to reversibly occlude the fluid conduit to atmosphere without an external control means disposed externally to the pressure regulator valve. An external control means may, for example, be an electrical control system comprising a sensor, electrically coupled to a control device which triggers the occlusion of the fluid conduit by, for example, gating the valve, switching the valve and/or triggering a transition for from the open state of the valve to the closed state. Where the sealing means is configured to reversibly occlude the fluid conduit without an external control means disposed externally to the pressure regulator valve the wound dressing tubing connector is advantageously simple in construction and operation.

An external control means may be responsive to feedback from an electrical sensing means.

Optionally, the passive control means comprises a biasing means for biasing a sealing means to seal said fluid conduit. The biasing means may be interposed between the sealing means and a means for supporting the biasing means. The biasing means may be compressible. For example the biasing means may be a spring element, a compressible foam element or a telescopic element.

The means for supporting the biasing means may be formed from a surface of the pressure regulator valve. Alternatively, the means for supporting biasing means may be formed from a surface of the first and/or second unit. The means for supporting the biasing means may be formed as part of the biasing means and attached to a surface of the pressure regulator valve and/or a surface of the first and/or second unit. The means for supporting the biasing means may extend into a recess within the biasing means. The means for supporting the biasing means may be of any suitable construction.

The sealing means may comprise a seal element and the biasing means comprises a spring element, which is configured to act against said seal element. Optionally, the sealing means is a seal element, the biasing means is a spring element and the means for supporting the biasing means is a spring locator. The pressure regulator valve may comprise a spring element and/or a seal element, and/or a spring locator.

Optionally, the pressure regulator valve comprises a valve seat element and wherein the seal element, the spring locator and/or the spring element, is/are disposed between the valve seat element and the fluid path and wherein the valve seat element and the seal element are at least partially exposed to the atmosphere. The pressure regulator valve may be orientated with the seal element on the outlet port to atmosphere.

The pressure regulator valve is optionally arranged adjacent the fluid path.

The pressure regulator valve may comprise a non-uniform boundary. A non-uniform boundary may advantageously prevent occlusion of the pressure regulator valve by an external object.

Optionally, the non-uniform boundary comprises an uneven surface, castellations, slots and/or openings.

Optionally, the uneven surface is provided on the valve seat element.

The pressure regulator valve may be a duck bill valve.

The pressure regulator valve may be arranged at any angle to the fluid path. Optionally, the pressure regulator valve is arranged substantially perpendicularly to the fluid path. Alternatively, the pressure regulator valve may be arranged at an angle to the fluid path, for example about 15°, about 30°, about 45°, about 60°, about 75°, about 80° or about 85°.

Optionally, the first unit and/or the second unit comprises more than one pressure regulator valve. Each pressure regulator valve may be independently connected to the fluid path directly or indirectly. The first unit may contain one or more pressure regulator valves. The second unit may contain one or more pressure regulator valves. The first unit and the second unit may contain one or more pressure regulator valves. The first unit and/or second unit may, for example, contain one, two, three or four pressure regulator valves. The incorporation of more than one pressure regulator valve may advantageously mitigate the negative effects of accidental occlusion or failure of one pressure regulator valve.

In embodiments where the connector comprises more than one pressure regulator valve, the fluid conduits, parallel paths and/or air paths from each pressure regulator valve may be independently arranged in fluid communication with the fluid path directly or indirectly. For example, when the pressure regulator valves are arranged in indirect fluid communication with the fluid path, the connector may comprise more than one parallel pathway. The connector may comprise a parallel pathway between each pressure regulator valve and the fluid path. The parallel pathways may merge before joining the fluid path. Alternatively, the parallel pathways may not merge and join the fluid path independently.

When the pressure regulator valves are arranged in indirect fluid communication with the fluid path, the connector may comprise more than one air path. The connector may be arranged so that each pressure regulator valve is in fluid communication with the fluid path via a separate air path.

Accordingly, the connector may comprise more than one air path. The air paths may merge before joining the fluid path. Alternatively, the parallel pathways may not merge and join the fluid path independently. When the air path is at least partially external to the connector, the site at which one or more air paths join the fluid path may be the wound dressing.

The first and/or second unit may therefore comprise one or more fluid couplings arranged to connect to one or more tubes for air.

Optionally, the first unit and/or the second unit comprise(s) two pressure regulator valves.

The first unit may comprise two pressure regulator valves.

The first unit may contain a pressure regulator valve in which a compression spring is fitted between the connector body and the valve seal by means of a locator.

The first unit may contain two pressure regulator valves in which a compression spring is fitted between the connector body and the valve seal by means of a locator.

The connector is releasably connectable by means of a male and female sealing system, a face sealing system, a magnetic latching system, an external locking collar, a twistlock barb system and/or a snap buckle system. The first unit and second unit may be connected by any suitable means. A male and female sealing system may comprise a male spigot and a female spigot. The male spigot and/or female spigot may be formed from the first unit and/or second unit.

The connector may be releasably connectable by means of a male and female sealing system and wherein the outlet of the first unit is configured to provide a male spigot and the inlet of second unit is configured to provide a female spigot. The first unit and second unit may be connected by a male and female sealing system wherein the first unit is a male unit and the second unit is a female unit. Alternatively, the first unit and second unit may be connected by a male and female sealing system wherein the first unit is a female unit and the second unit is a male unit.

Optionally, the air and fluid tight seal is provided by means of one or more of a spring, a gasket or an O-ring, interposed between the first unit and the second unit. The O-ring, spring or gasket may be of any suitable construction. The seal may prevent the flow of air or fluid from the atmosphere into or out of the connector. The seal may prevent the flow of air or fluid from fluid path out of the connector.

A connector of the invention is provided which optionally further comprises a first tube connected to the inlet of the first unit.

A connector of the invention is provided which optionally further comprises a second tube connected to the outlet of the second unit.

A connector of the invention is provided which optionally further comprises one or more further tubes connected to the one or more fluid couplings of the first and/or second unit. The fluid couplings may be arranged to connect to one or more tubes for air.

The first tube, the second tube and/or the one or more further tubes may be present in any combination.

The device may be in a Y-configuration in which the first unit comprises an inlet and an outlet and the second unit comprises an inlet and two outlets, or the configuration may be reversed such that the first unit may comprise two inlets and one outlet and the second unit comprises one inlet and one outlet. Where the fluid path is divided into two paths, either the fluid path in the first unit is divided and comprises two inlets, or the fluid path in the second unit is divided and comprises two outlets.

The connector may comprise one or more indicator elements configured to provide an indication when the pressure within the fluid path reaches a pre-determined level. This level may be a maximum or minimum pressure value. Two indicators may be included to show both minimum and maximum levels. A first indicator may show the maximum pressure value and a second indicator may show the minimum pressure value.

The mechanism to achieve an indication of when the pressure within the fluid path reaches a pre-determined level may include a biased poppet or diaphragm arrangement configured to actuate at the pre-determined pressure level. Accordingly, the one or more indicator elements may comprise a biased poppet or diaphragm arrangement configured to actuate at the pre-determined pressure level.

The indication provided by the indication element may be visual or non-visual.

The indication element may further comprise a coloured disc or button configured to provide a visual indication when the pressure within the fluid path reaches a pre-determined level, for example by lighting up, changing colour or moving from a first position to a second position.

Alternatively the indication element may further comprise an electrical contact that provides a non-visual indication when the pressure within the fluid path reaches a pre-determined level, for example by communicating with a control system. Accordingly, the non-visual indication may be an electronic signal, which may be transmitted from the indication element to the control system.

In other embodiments of the invention, the first unit and the second unit may be fused together or manufactured as a single unit.

According to a second aspect of the invention there is provided a system for applying sub-atmospheric pressure to a wound dressing comprising a connector in accordance with the first aspect, a vacuum source and a wound dressing, wherein the vacuum source is in fluid communication with the wound dressing via the connector.

A system is also provided for use in negative pressure wound therapy comprising the wound dressing fluid connector of the first aspect, connected to a dressing via the first tube.

A system is also provided for use in negative pressure wound therapy comprising the wound dressing fluid connector of the first aspect connected to a vacuum source via the second tube.

The system optionally further comprises one or more further tubes connected to one or more fluid couplings of the first and/or second unit. The fluid couplings may be arranged to connect to one or more tubes for air.

The vacuum source may be any suitable negative pressure source. For example, the vacuum source may be a peristaltic pump, a hospital wall suction device, a portable suction device, a bellows suction device or a suction device powered by a spring means.

The dressing may be of any suitable construction for treatment of a wound using NPWT. For example, the dressing may be a pad for placing in the wound composed of reticulated open cell foam, gauze, and/or an absorbent dressing material.

According to a third aspect of the invention there is provided a wound dressing tubing connection kit comprising the first unit in accordance with the first unit of the first aspect, a first tube, wherein the first tube is connectable to an outlet of a wound dressing and the inlet of the first unit, and optionally further comprising the wound dressing.

The wound dressing tubing connection kit optionally further comprises one or more further tubes connected to one or more fluid couplings of the first and/or second unit. The fluid couplings may be arranged to connect to one or more tubes for air.

The first unit of this aspect may be the first unit as described anywhere in connection with the first aspect of the invention.

In some embodiments the wound dressing tubing connection kit of this aspect does not comprise the wound dressing. In other embodiments, the wound dressing tubing connection kit of this aspect comprises the wound dressing.

The kit may further comprise the second unit. The second unit of this aspect may be the second unit as described anywhere in connection with the first aspect of the invention.

According to a fourth aspect of the invention there is provided a wound dressing tubing connection kit comprising the second unit in accordance with the second unit of the first aspect and a second tube, wherein the second tube is connectable to the outlet of the second unit and the inlet of a vacuum source.

The wound dressing tubing connection kit optionally further comprises one or more further tubes connected to one or more fluid couplings of the first and/or second unit. The fluid couplings may be arranged to connect to one or more tubes for air.

The second unit of this aspect may be the second unit as described anywhere in connection with the first aspect of the invention.

The kit may further comprise the first unit. The first unit of this aspect may be the first unit as described anywhere in connection the first aspect of the invention.

The kit may further comprise the vacuum source. The vacuum source of this aspect may be the vacuum source as described in connection with any other aspect of the invention.

According to a fifth aspect of the invention there is provided a wound dressing tubing connection kit comprising a wound fluid connector the first aspect of the invention, a first tube, wherein the first tube is connectable to an outlet of a wound dressing and the inlet of the first unit, a second tube, wherein the second tube is connectable to the outlet of the second unit and the inlet of a vacuum source, and optionally further comprising the wound dressing.

In some embodiments the wound dressing tubing connection kit of this aspect does not comprise the wound dressing. In other embodiments, the wound dressing tubing connection kit of this aspect comprises the wound dressing.

The wound dressing tubing connection kit optionally further comprises one or more further tubes connected to one or more fluid couplings of the first and/or second unit. The fluid couplings may be arranged to connect to one or more tubes for air.

The kit may further comprise the vacuum source. The vacuum source of this aspect may be the vacuum source as described in connection with any other aspect of the invention.

According to a sixth aspect of the invention there is provided a method of treatment of a subject in need thereof, comprising the steps of applying a wound dressing to a wound and connecting the wound dressing to a fluid container via a connector according to the first aspect of the invention, wherein the wound is kept under negative air pressure. The negative air pressure can be provided by connecting the fluid container to a source of a vacuum or a suitable pump.

According to a seventh aspect of the invention there is provided a method of treatment of a subject in need thereof, comprising the steps of applying a wound dressing connected to a fluid container via a connector according to the first aspect of the invention to a wound, wherein the wound is kept under negative air pressure. The negative air pressure can be provided by connecting the fluid container to a source of a vacuum or a suitable pump.

The invention optionally utilises a mechanical positive pressure regulator fitted in reverse that opens when the negative pressure reaches a predetermined level causing the seal to open allowing air at atmospheric pressure to enter thus maintaining the negative pressure at the wound site within the desired range.

Additionally through testing it has been shown that controlling the pressure close to the wound site is desirable in terms of accuracy and reducing the pressure differential between the wound site and the pump unit due to the effects of hydrostatic head pressure as fluid is pulled upwards by up to a metre in the case of a foot wound.

However housing a mechanical valve close to the wound site, for example in the dressing, has potential risks in damaging the already compromised skin. This invention is aimed to overcome these disadvantages by incorporating the valves in the connector that couples the dressing to the fluid container. This connector is required because there is a different frequency of dressing changes to fluid container changes.

The present invention therefore seeks to provide:

Accurate pressure control at the wound without the need for multiple tubes and sensors to the wound site and the associated level of complexity in the electronic control system and software.

Incorporation of a NPWT device into the connector that is close to the wound site which reduces head pressure differences.

A means to allow fluid to be drawn away from the wound at a constant flow preventing the fluid "pooling" at the wound site.

A valve system which prevents the fluid from escaping from the tube set and dressing when therapy is turned off because the seals are normally closed.

A system with an optimum size and minimises potential for skin damage.

A key advantage of the present invention is that it seeks to address the fundamental problems associated with NPWT treatment (which was originally developed for the hospital market) for use in the home and community market.

The present invention seeks to provide a means of delivering NPWT effectively at the wound site in a very simple form without the need for expensive electronics.

The accuracy of the pressure control at the wound can be high because it is directly controlled.

The pressure control means seeks to allow the fluid to be constantly aerated at the wound site allowing the fluid to be effectively withdrawn from the wound site reducing the risk of "pooling" and the associated risks i.e. maceration, infection etc.

The use of this design of valve i.e. a pressure regulator valve in reverse seeks to provide an effective means of sealing the dressing against fluid leakage when the negative pressure is removed.

The means of controlling pressure at the wound site seeks to allow alternative pump type systems to be used such as Positive Displacement Pumps which include peristaltic pumps. Previously these could not be used without wound site pressure control because the sealed nature of these systems means that pressure at the wound site cannot be controlled by reducing speed of the pump as is the case with conventional air pumps.

The direct pressure control seeks to allow other vacuum sources to be used that previously could not be used because they require regulation at source, this includes wall suction or potentially a mechanical means such as bellows or sprung loaded vacuum generation device.

Provided the vacuum source is higher than the required wound site target pressure then the pressure regulator valve at the dressing will maintain the correct pressure at the wound.

The pressure can be maintained at the wound site without the complexity of multiple pressure sensors, signal conditioning circuitry and pressure control algorithms. Overall cost, size and weight can be reduced.

The direct nature of the pressure control at the wound site results in a very efficient use of the vacuum source because the rest of the system can be air tight resulting in very low noise and very low power consumption.

The configuration of a mechanical pressure regulation valve is fundamental when a peristaltic pump is used to generate a negative pressure as conventional methods of controlling pressure by slowing the pump down does not work.

The configuration of a pressure regulation valve with a peristaltic pump could be used with both a conventional style dressing where fluid is removed from the wound site into a waste container or it could be used in conjunction with a super absorbent dressing placed at the wound site. In this configuration the pump generates a negative pressure within an encapsulated wound dressing and the valve maintains it at the pre-set pressure but fluid is not removed from the wound site and is absorbed into the dressing by virtue of super-absorbent materials and barrier films.

Where the pressure regulator valve may be connected to the fluid path via a separate conduit that runs in parallel to the fluid path and interconnects to the fluid path exterior to the connector at the wound site and/or the connector comprises one or more fluid couplings, pressure regulation may occur directly at the wound site as opposed to indirectly through the fluid path.

A separate air pathway allows air to pass into the wound site. This may be advantageous to aerate the wound or stimulate the fluid removal via the fluid path as a positive air pressure will force fluid from the wound into the fluid path.

Air entering the wound may have the additional advantage of oxygenating the wound.

Several aspects of the invention are believed not to be obvious for the following reasons:

The use of a standard type pressure regulator originally intended for a pneumatic application is used in reverse with the intended outlet port orientated on the fluid side of the dressing.

The use of an air pressure regulator valve to act as a check valve when fitted in the reverse orientation and subjected to fluid pressure on the normal outlet Valves have been incorporated into connectors to prevent fluid seeping out i.e. shut off valves but not as a pressure regulation system Size and technical difficulties in incorporating valves into a miniature connector, this has been possible by the arrangement of regulator valve set at 90 degrees to the fluid flow The use of a bayonet system with a compressible seal on the flow allows space to be minimised whilst the seal has a dual purposes of sealing the fluid and providing a small force to lock the bayonet in place Preferred features of the second and subsequent aspects are as for the first aspect mutatis mutandis.

The invention will now be described by way of example with reference to the following drawings in which:

FIG. 1 shows a cross-sectional view of a connector as separate male and female units before connection.

FIG. 2 shows a cross-sectional view of a connector after separate male and female units are connected with operation under normal conditions.

FIG. 3 shows a cross-sectional view of a connector with separate male and female units connected with operation under conditions where internal negative pressure has reached a level equivalent or greater than the compressive force exerted by the spring means.

FIGS. 4, 5 and 6 show embodiments of the invention in which two valves are present.

Figure 7:
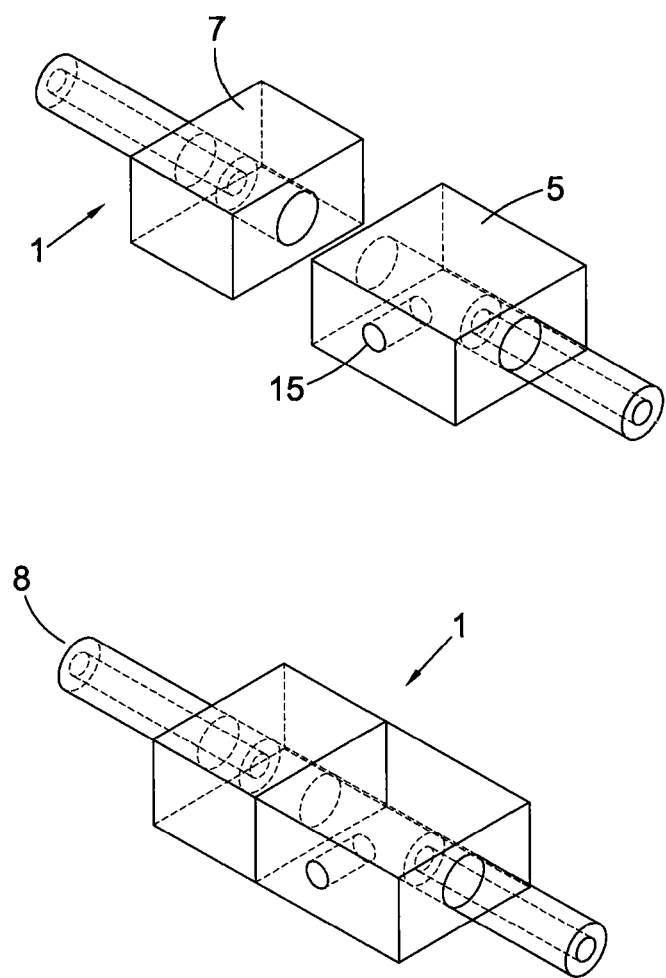
FIG. 7 is an isometric view of a wound dressing tubing connector (1) of the invention.

As shown in FIG. 1, wound dressing tubing connector (1) consists of first unit or dressing side (connector) half (5) configured as a male spigot to which tube (3) is fitted. The second unit or pump side (connector) (7) is configured as a female spigot and consists of tube (11) fitted to the connector in which region (9) is connectable to the first unit.

First and second connector units (5) and (7) can be mated via a latching mechanism to form a continuous internal path (25) and an air tight seal. Tube (3) typically will be connected to a wound dressing and tube (11) to a pumping mechanism or vacuum source (12).

O-ring (13) provides and air tight seal between connector halves (5) and (7), additionally providing an opposing force when it is compressed by connector region (9) that exerts a constant frictional force between the two connector halves which reduces the risk of accidental disconnection.

Wound dressing tubing connector (1) has an integrated valve body (15). Valve body (15) accommodates a compression spring (17) which acts between spring locator (19) and valve seal (21). This arrangement allows seal (21) to press against the valve seat (23) thus sealing the inside of the connector assembly and tubing from atmospheric pressure.

In normal conditions as shown in FIG. 2, fluid or air passes through internal path (25) at the pressure determined by the pump or vacuum source (12). As shown in FIG. 3, once the internal negative pressure reaches a level that is equivalent or greater than the compressive force exerted by spring (17), the atmospheric air will overcome the spring force and air will enter the connector by bypassing seal (21) creating a fluid conduit (27). This will have the effect of lowering the internal negative pressure until equilibrium is restored by the spring force exerted by the spring (17).

In normal operation a seal is obtained between the negative pressure source (12) which is connected either directly or indirectly to (7) and this in turn is connected to a sealed wound dressing. Fluid is drawn up the fluid path (25) away from the wound site towards the negative pressure source (12). In order to regulate the pressure at a pre-determined level, a valve (15) is connected to one or both halves of the connector. This valve (15) provides a means of air at atmospheric pressure entering the fluid conduit (27) and reducing the negative pressure in the connector and subsequently at the wound site.

Various configurations of connectors are possible including those that have a twist bayonet action in order to lock the mating halves (5) and (7) together. Other configurations include a buckle style system and twist lock system such as used in a Luer lock device. A seal is used in the form of an O-ring or a gasket between the two halves to ensure atmospheric air does not enter the connector in an uncontrolled manner and also to prevent fluid leaks from the fluid path (25).

Due to the arrangement of the valve(s) body (15), fluid is free to flow unimpeded through pathway (25) irrespective of the action of the valve. A non-uniform boundary, for example, an uneven surface, castellations, slots or openings can be provided on valve body (15) to prevent the air entry into the connector from becoming blocked.

FIGS. 4, 5 and 6 show the invention with two valves as an alternative embodiment. The advantage of two valves over one is that it reduces the risk of the system failing due to a valve blockage.

The connector halves (the male unit and the female unit) are mated using a latching mechanism to provide a continuous internal path for fluid or air and to seal the internal path from atmospheric air.

The latching mechanism consists of a barbed arrangement that locks in place when the two halves are rotated in an opposing direction. The O-ring provides a compression force that prevents the two halves accidentally becoming undone.

Other latching mechanisms may be employed including Luer-lock type connector systems, screw threads, buckle style snap fits or ball detent systems.

FIG. 7 is a diagrammatic representation in isometric view of a wound dressing tubing connector (1) of the invention.

Figure 8:
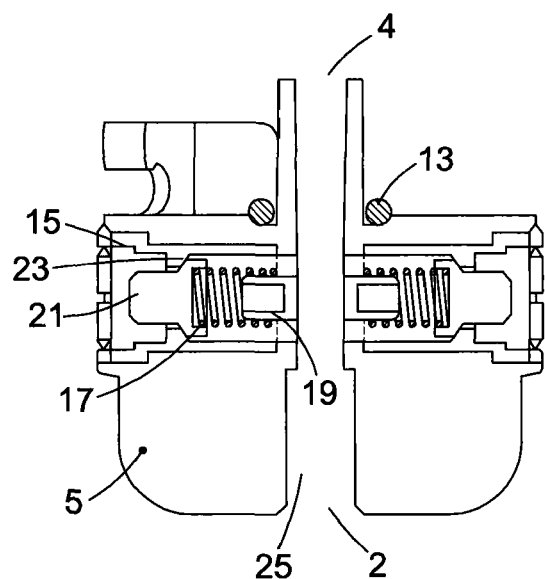
FIGS. 8 and 9 show specific embodiments of the invention.

FIG. 8 shows a first unit (5) of the invention configured as a male spigot. The first unit (5) of FIG. 8 may be connected as shown in FIG. 9 to a second unit (7) configured as a female spigot using a twist bayonet action.

Figure 9:
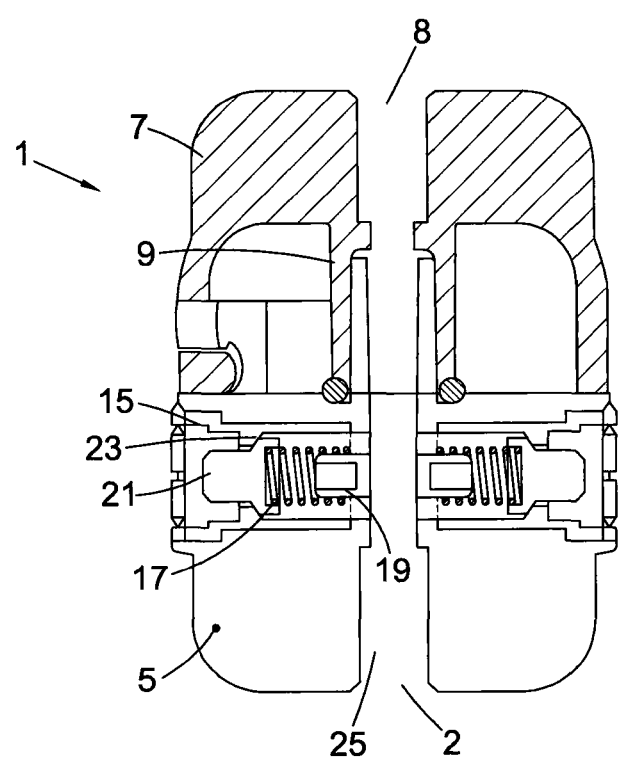

FIG. 9 shows connector (1) which consists of two mating halves (5) and (7) which are connected to form an air and fluid tight seal.

In order to control the pressure in a controlled manner a pressure regulating valve (15) is required as shown in FIG. 1. One configuration of this valve is shown in FIGS. 8 and 9, in which the valve body (15) is fitted into a cavity within the connector body (5), compression spring (17) is fitted between the connector body and valve seal (21). When the pressure inside the fluid path (25) is equivalent to pressure outside the conduit path then the valve seal (21) is closed due to the positive pressure of the spring (17), this prevents air at atmospheric pressure entering the connector or fluid leaking out of the connector. When the pressure in fluid path (25) reaches a differential pressure to atmospheric pressure that is equivalent to the positive force of the spring, the spring force will be overcome and atmospheric air will enter the connector to equalise the pressure. By this configuration the selection of spring rate can control the negative pressure within the connector to provide accurate therapeutic pressure at the wound site and aid the removal of fluid whilst ensuring it does not leak out of the connector. In this example an O-ring (13) provides the means of ensuring a seal between the fluid conduit path on both halves of the connector.

In the example illustrated in FIGS. 8 and 9 two valves are incorporated into a single connector body to provide an additional safety feature if one valve should malfunction or become blocked.

Alternative configurations include arranging the valves in a Y configuration.

Alternative sealing systems to the male and female sealing system may be employed including a face sealing system, an external locking collar and/or a magnetic latching system. The alternative sealing systems may be implemented by use of connector halves that do not have a male and female spigot but are coupled by alternative means such as face sealing utilising a barb latch, external rotating collar or magnetic sealing. Any of the above sealing systems may be used in conjunction with a male and female sealing system and/or the latching systems described above or as alternatives thereto.

Figure 10:
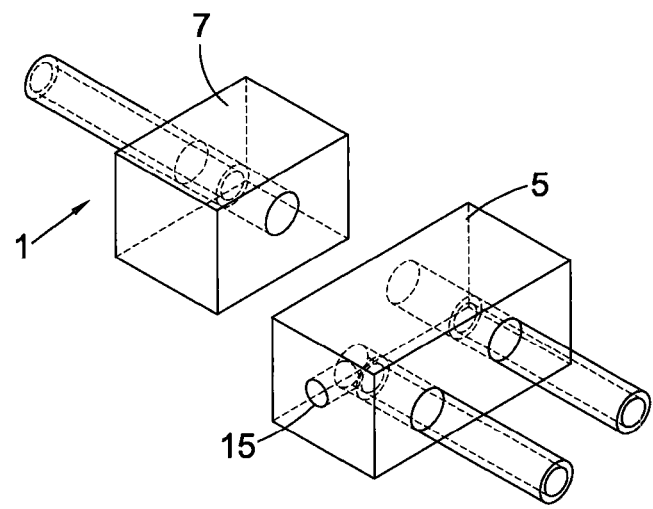
FIG. 10 is an isometric view of a wound dressing tubing connector (1) of the invention in which the pressure regulator valve is connected indirectly to the fluid path.
Figure 10:
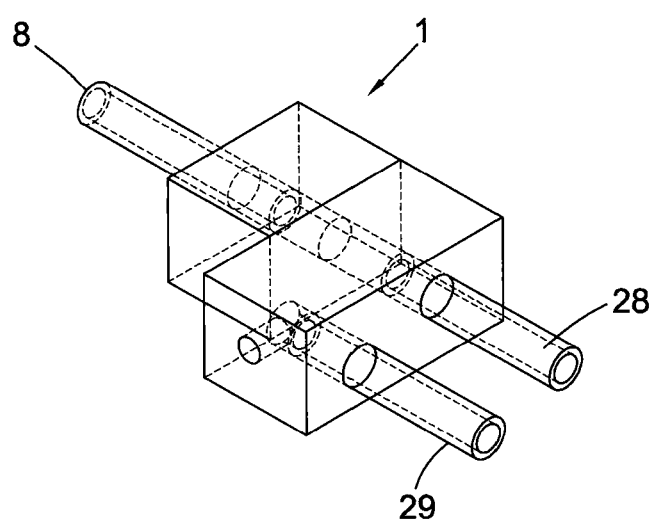

FIG. 10 is a diagrammatic representation in isometric view of a connector (1) where the pressure regulator valve (15) is connected to the fluid path (28) via a separate conduit, an air pathway (29) that runs in parallel to the fluid path (28) and may interconnect to the fluid path (28) remotely from the connector or separately, for example at the wound site. The fluid inlet tube (28) extends between the wound dressing and the first unit (5) of the connector. The air pathway (29) may extend between the pressure regulator valve and the wound dressing (not shown). The distal end of the fluid inlet tube (28) may terminate at the wound dressing and allows air from the air pathway (29) to enter the wound site. The outlet (8) extends between the second unit (7) of the connector and the pump. When the first unit (5) is attached to the second unit (7) a fluid path through the connector is formed.

The following example is provided also for the purposes of illustration only and is not to be construed as being limiting on the invention.

Experiment 1: Testing the Connector

With a closed system (air only) utilising a peristaltic pump it was demonstrated that the pressure could not be controlled adequately, as the pump speed increased the pressure correspondingly increased to in excess of 350 mmHg. Decreasing the pump speed did not effectively reduce the pressure and it remained at over 200 mmHg even at the lowest setting used of 5 RPM. Any pressure decrease was only due to connector leakages and the breathability of the drape.

With the proposed pressure valve fitted at the dressing site at full speed of 200 mmHg the wound site pressure was limited to 125 mmHg+/−25 mmHg with a momentary maximum of 150 mmHg as the valve initially opened.

With fluid introduced at 30 rpm a constant flow rate was achieved. The fluid flow was aided by small amounts of air being drawn through the valve which allowed mobility of the fluid from the dressing to the container.

Changing the height of the dressing relative to the pump (0.5 metres) did not result in any measurable pressure change at the wound-site.

Results

A standard pressure control valve was used in the reverse orientation i.e. the normal outlet to atmosphere was connected to the fluid side, the variance of negative pressure readings was well within the stated manufacturers tolerance of +/−20%, which would normally relate to a total tolerance of 25 mmHg at the normal working pressure. The pressures measured after the valve originally opened and the pressure stabilised to be in the order of 10 mmHg total working tolerance.

This is believed to be significantly more accurate than electronic control systems that rely on multiple conduit pathways and multiple electronic components.

The introduction of the pressure valve had a second effect beyond pressure control that was not anticipated, this was to allow the introduction of small amounts of air into the system at the dressing site. This had two effects, the first was to allow constant flow of fluid from the dressing at a very low flow rates, the second was to provide a mechanism to reduce pressure at the wound site when sealed pump systems such as a peristaltic pump is used. Additionally the valve had the effect of aerating the fluid evenly causing mobility which appeared to be different in nature when a basic leak is introduced through an orifice. One explanation for this may be due to the design of the valve and the characteristics of the sprung loaded component and seat, although this valve is designed to relieve positive air pressure it has an advantageous effect in regulating air inflow under negative pressure when fitted in reverse. A second major advantage of the valve arrangement is due to the reverse nature of the sprung loaded action when fluid is forced back into the dressing the valve will be forced closed effectively sealing the dressing. Several scenarios exist when this can happen; one example is when therapy is paused for when the patient is taken a shower, in this case gravity or pressure against the dressing could cause fluid to pool in the dressing, and normally if the dressing contained any passage to atmosphere then fluid could leak out causing an infection risk.

In the case of devices that contain sensing tubes or conduits to the control unit to control pressure these can potentially fill with fluid when negative pressure is paused that may cause blockages, this situation is eliminated in the present invention.

The invention claimed is:

1. A wound dressing tubing connector comprising a first unit and a second unit which are releasably connectable and which when connected form a fluid path through the connector wherein the first unit comprises an inlet and an outlet and the second unit comprises an inlet and an outlet, in which the outlet of the first unit and the inlet of the second unit when the first and second unit are connected together define the fluid path, and wherein the first unit and the second unit are connectable to form an air and fluid tight seal; and
    wherein the first unit and/or the second unit comprises:
    a connector body having a fluid-flow bore of fixed lateral extent extending between the said inlet and the said outlet, the fluid-flow bore forming at least part of the said fluid path;
    the said connector body having a tube-receiver portion at one end thereof to receive an end of a wound-dressing tube;
    the said connector body having a pressure regulator valve which is spaced from the tube-receiver portion along the fluid flow bore;
    the pressure regulator valve having a valve body which extends from a side of the fluid flow bore;
    the said valve body having a valve bore which intersects with the said fluid-flow bore, such that the pressure regulator valve is in fluid communication with the said fluid path;
    the pressure regulator valve having a valve seal and a spring which are in the said valve body to close the said valve bore;
    the spring is configured to act against the valve seal to close the pressure regulator valve when the pressure in the fluid path reaches a differential pressure relative to atmospheric pressure that is greater than or equal to the positive force of the spring, the pressure regulator valve being configured such that when the pressure in the fluid path is sufficiently low, whereby a differential pressure created relative to atmospheric pressure is equivalent to the positive force of the spring, the spring force is overcome to release the valve seal so that atmospheric air enters the valve bore and flows over the said spring along the valve bore to the said fluid flow bore in order to equalise the pressure in the fluid path.

2. The connector according to claim 1, wherein the pressure regulator valve is arranged adjacent the fluid path.

3. The connector according to claim 1, wherein an outlet of the fluid conduit is provided with a non-uniform boundary comprising an uneven surface, castellations, slots and/or openings.

4. The connector according to claim 3, wherein the non-uniform boundary is provided on a valve seat element.

5. The connector according to claim 1, wherein the pressure regulator valve is arranged substantially perpendicularly to the fluid path.

6. The connector according to claim 1, wherein the first unit and/or the second unit comprises more than one pressure regulator valve.

7. The connector according to claim 1, wherein the valve is provided in the fluid conduit.

8. The connector according to claim 1, wherein the connector is releasably connectable using a bayonet twist sealing system.

9. The connector according to claim 8, wherein the connector is releasably connectable by means of a male and female sealing system and wherein the outlet of the first unit is configured to provide a male spigot and the inlet of second unit is configured to provide a female spigot.

10. The connector according to claim 1, wherein the air and fluid tight seal is provided by means of one or more of a spring, a gasket or an O-ring, interposed between the first unit and the second unit.

11. The connector according to claim 1, further comprising a first tube connected to the inlet of the first unit.

12. The connector according to claim 1, further comprising a second tube connected to the outlet of the second unit.

13. A system for applying sub-atmospheric pressure to a wound dressing comprising a connector of claim 1, a vacuum source and a wound dressing, wherein the vacuum source is in fluid communication with the wound dressing via the connector.

14. A wound dressing tubing connection kit comprising:
    (a) the wound fluid connector of claim 1,
    (b) a first tube, wherein the first tube is connectable to an outlet of a wound dressing and the inlet of the first unit,
    (c) a second tube, wherein the second tube is connectable to the outlet of the second unit and optionally,
    (d) the wound dressing.

15. The kit of claim 14, further comprising a vacuum source having an inlet, the second tube being connectable to the inlet of the vacuum source.

16. The kit of claim 15, wherein the vacuum source is a peristaltic pump, a hospital wall suction device, a portable suction device, a bellows suction device or a suction device powered by a spring means.

17. The connector according to claim 1, wherein the pressure regulator valve comprises only one said spring.

18. The kit of claim 14, wherein the wound dressing comprises a pad for placing in the wound composed of reticulated open cell foam, gauze, and/or an absorbent dressing material.

19. A wound dressing tubing connector comprising a first unit and a second unit which are releasably connectable and which when connected form a fluid path through the connector wherein the first unit comprises an inlet and an outlet and the second unit comprises an inlet and an outlet, in which the outlet of the first unit and the inlet of the second unit when the first and second unit are connected together define the fluid path, and wherein the first unit and the second unit are connectable to form an air and fluid tight seal; and wherein the first unit and/or the second unit comprises a pressure regulator valve in fluid communication with the fluid path;

the pressure regulator valve having a valve seat element, a valve seal and a spring, the valve seal and spring being located between the valve seat element and an inlet to the fluid path;

wherein the spring is configured to act against the valve seal to close the pressure regulator valve when the pressure in the fluid path reaches a differential pressure relative to atmospheric pressure that is greater than or equal to the positive force of the spring, the pressure regulator valve being configured such that when the pressure in the fluid path is sufficiently low, whereby a differential pressure created relative to atmospheric pressure is equivalent to the positive force of the spring, the spring force is overcome and atmospheric air enters the connector to equalise the pressure in the fluid path.

* * * * *